(12) United States Patent
Shurgalin

(10) Patent No.: US 11,291,504 B1
(45) Date of Patent: Apr. 5, 2022

(54) METHOD OF INCISING AND ABLATING LIVING TISSUES AND SURGICAL LASER DEVICES

(71) Applicant: Max Shurgalin, Bedford, MA (US)

(72) Inventor: Max Shurgalin, Bedford, MA (US)

( * ) Notice: Subject to any disclaimer, the term of this patent is extended or adjusted under 35 U.S.C. 154(b) by 0 days.

(21) Appl. No.: 17/221,796

(22) Filed: Apr. 3, 2021

(51) Int. Cl.
*A61B 18/22* (2006.01)
*A61B 18/04* (2006.01)
*A61B 18/00* (2006.01)
*A61B 18/20* (2006.01)
*A61B 17/00* (2006.01)

(52) U.S. Cl.
CPC ............. *A61B 18/22* (2013.01); *A61B 18/04* (2013.01); *A61B 2017/00181* (2013.01); *A61B 2018/00577* (2013.01); *A61B 2018/00607* (2013.01); *A61B 2018/00714* (2013.01); *A61B 2018/00761* (2013.01); *A61B 2018/00994* (2013.01);

(Continued)

(58) Field of Classification Search
CPC .................. A61B 18/22; A61B 18/04; A61B 2018/20351; A61B 2017/00181; A61B 2018/00577; A61B 2018/00607; A61B 2018/00761; A61B 2018/00994; A61B 2018/2227; A61B 2018/00571–00577; A61B 2018/006544; A61B 2018/00714–00767; A61B 2018/0091

See application file for complete search history.

(56) References Cited

U.S. PATENT DOCUMENTS 4,273,127 A  6/1981 Auth
4,573,465 A * 3/1986 Sugiyama .............. A61B 18/20
                                                    219/121.76

(Continued)

FOREIGN PATENT DOCUMENTS

EP    0993086 A2    4/2000
EP    2386262 A1    11/2011
EP    3512448 B1    3/2021

OTHER PUBLICATIONS

Filatova et. el., "Optical properties of animal tissues in the wavelength range from 350 to 2600 nm", Journal of Biomedical Optics, vol. 22, 035009, Mar. 2017, SPIE digital library, p. 035009-3, figure 2.

(Continued)

*Primary Examiner* — Oommen Jacob

(57) ABSTRACT

A method and laser surgical devices for surgical incising and ablating living tissues using laser beam and effecting enhanced surgical haemostasis concurrently with incising and ablating are disclosed. The method requires a surgical laser beam that is pulsed and is highly absorbed in living tissues and enhanced haemostatic action is achieved using along with the surgical laser beam energy, delivered in pulses, another separately controlled energy effecting haemostasis, by applying the second energy in any and every given spot of incising and ablating in a preemptive and focused manner, which minimizes haemostasis-related damage to surrounding tissues. In one embodiment a heated gas jet from a hollow core optical fiber transmitting the surgical laser beam is used. In other embodiments an ancillary laser radiation at a wavelength chosen specifically to minimize haemostasis-related damage to tissue is utilized for preemptive and controlled haemostatic effect.

19 Claims, 7 Drawing Sheets

(52) U.S. Cl.
CPC ............... *A61B 2018/048* (2013.01); *A61B 2018/20351* (2017.05); *A61B 2018/2227* (2013.01)

(56) References Cited

U.S. PATENT DOCUMENTS

| | | | |
|---|---|---|---|
| 5,139,494 A | 8/1992 | Freiberg | |
| 5,190,535 A | 3/1993 | Daikuzono | |
| 5,312,399 A * | 5/1994 | Hakky | A61B 17/320758 606/14 |
| 5,325,393 A * | 6/1994 | Nighan, Jr. | H01S 3/2383 372/23 |
| 5,571,098 A | 11/1996 | Domankevitz | |
| 5,695,493 A | 12/1997 | Nakajima | |
| 5,873,875 A * | 2/1999 | Altshuler | A61C 1/0046 606/10 |
| 6,110,165 A | 8/2000 | Ota | |
| 6,258,082 B1 * | 7/2001 | Lin | A61F 9/008 372/37 |
| 6,463,083 B1 | 10/2002 | Sumiyoshi | |
| 8,876,810 B2 * | 11/2014 | Neuberger | A61B 18/24 606/16 |
| 8,881,735 B2 * | 11/2014 | Mitchell | A61B 34/25 128/898 |
| 8,888,767 B2 * | 11/2014 | Neuberger | A61B 18/042 606/15 |
| 9,044,255 B2 * | 6/2015 | Kang | H01S 3/1643 |
| 9,445,871 B2 * | 9/2016 | Kang | H01S 3/1068 |
| 9,844,410 B2 * | 12/2017 | Mitchell | A61B 34/25 |
| 9,895,560 B2 * | 2/2018 | Barthe | A61N 7/02 |
| 9,993,664 B2 * | 6/2018 | Aviad | A61B 18/203 |
| 10,413,362 B2 | 9/2019 | Griffin | |
| 2001/0016732 A1 * | 8/2001 | Hobart | A61B 18/203 606/2 |
| 2002/0133149 A1 * | 9/2002 | Bessette | A61B 18/14 606/41 |
| 2004/0073202 A1 * | 4/2004 | Illich | B23K 26/0096 606/16 |
| 2005/0154380 A1 * | 7/2005 | DeBenedictis | A61B 18/203 606/9 |
| 2006/0259021 A1 * | 11/2006 | Lin | A61F 9/00821 606/4 |
| 2007/0031777 A1 * | 2/2007 | Wang | A61C 19/004 433/29 |
| 2007/0219601 A1 * | 9/2007 | Neuberger | A61B 18/24 607/89 |
| 2008/0058629 A1 * | 3/2008 | Seibel | A61B 1/00172 600/368 |
| 2008/0147150 A1 * | 6/2008 | Xiong | A61B 18/22 607/93 |
| 2011/0224660 A1 * | 9/2011 | Neuberger | A61B 18/22 606/15 |
| 2012/0078160 A1 * | 3/2012 | McMillan | A61N 5/0603 604/20 |
| 2013/0035684 A1 | 2/2013 | Neuberger | |
| 2013/0190738 A1 * | 7/2013 | Lukac | A61N 5/0624 606/10 |
| 2014/0012077 A1 * | 1/2014 | Fagnani | A61B 18/22 600/108 |
| 2015/0305811 A1 * | 10/2015 | Neuberger | A61N 5/0616 606/11 |
| 2017/0325886 A1 | 11/2017 | Graham | |

OTHER PUBLICATIONS

Anastassiou et. el. "Photonic Bandgap Fibers exploiting omnidirectional Reflectivity enable flexible Delivery of infrared Lasers for Tissue Cutting", Proceedings of SPIE, vol. 5317 (SPIE, Bellingham, WA, 2004), p. 34, figure 5.

* cited by examiner

METHOD OF INCISING AND ABLATING LIVING TISSUES AND SURGICAL LASER DEVICES

CROSS-REFERENCE TO RELATED APPLICATIONS

Not Applicable.

TECHNICAL FIELD

The present invention generally relates to devices used in laser surgeries, and specifically to technologies that make possible executing concurrently with incising and ablating living tissues with a laser beam greater control of bleeding while reducing associated with haemostasis injury to nearby healthy tissues, and without requiring surgical instrument to be in contact with a living tissue.

BACKGROUND OF THE INVENTION

Lasers became well-established instrument in surgical practice, often cited as preferred tool for precision surgery and microsurgery, where surgical accuracy enabling retention of most healthy tissues and organ function is of highest benefit to a patient. In laser procedures, as in any surgery, bleeding caused by cutting through blood vessels and capillaries must be minimized to prevent the adverse physiologic effects associated with blood loss. Control of bleeding during surgery, meaning stoppage or reduction of bleeding, is termed surgical haemostasis and a number of methods for effecting surgical haemostasis, including mechanical haemostatic techniques and thermal energy or tissue coagulation methods, can be utilized when haemostatic action of surgical laser beam energy alone is insufficient These methods in most cases require physical contact with living tissue and often require changing or adding an additional instrument. For example, widely used bipolar electrosurgical energy instrument for stopping bleeding is a contact mode device and it is often used together with laser cutting and ablating device. In small and tight surgical spaces, where two separate instruments may not fit in, cutting and ablating device, such as laser beam delivery handpiece, has to be interchanged with haemostasis device. Clearly a need exists in surgical practice to combine precision incising and ablation capability afforded by a surgical laser beam with enhanced and separately controlled haemostasis capability in one instrument and perform both tissue incision and ablation and better control of bleeding concurrently, not necessarily simultaneously as it may not be possible, thus reducing blood loss between instrument changes as well as removing a burden of frequent instrument changes. Desired is a technique of incising and ablating living tissues with laser precision and effecting appropriate surgical haemostasis while minimizing the spread of damage to healthy tissues and anatomical structures in need of preservation, and which is implemented in a single surgical device.

A laser-based method of cutting and coagulating tissue was disclosed in U.S. Pat. No. 4,273,127. Laser radiation is utilized to coagulate tissue next to the cutting edge of an instrument similar to a surgical scalpel and that way to create haemostatic effect. The extent of tissue coagulation is determined by the laser wavelength and the intensity of the laser radiation while the location of tissue coagulation automatically coincides with the incision because the laser radiation energy is transmitted into tissue from the device working edge. The approach is lacking both the contact-less nature and precision of laser beam because it relies on a cutting instrument very much like a traditional scalpel.

An approach to bring together in one device precision laser cutting and haemostatic capabilities was disclosed in U.S. Pat. No. 5,190,535, where the laser light is coupled into a special probe designed to radiate laser beam out of the tip to perform surgical incisions and out of the probe sides to induce haemostasis upon contact with tissue. Another related approach was presented in U.S. Pat. No. 5,695,493, where laser light is used to heat a small tip of a surgical probe and the hot tip is used to both incise and coagulate tissue. In both cases the disadvantages of such devices, relying on close contact with tissue, are poor reliability and consistency of interaction with tissues because the contact mode of operation causes contamination of probe surfaces affecting laser energy transmission as well as deterioration and optical damage of the probe itself.

Recently a combination handpiece device was disclosed in US patent application 2017/0325886. In that device laser radiation is delivered via optical fiber or waveguide inserted into the handpiece and used to perform laser surgery. The handpiece itself has integrated bipolar electrosurgical electrodes used for surgical haemostasis. No instrument changes are required when switching from laser cutting and ablation to control of bleeding with built-in bipolar electrosurgical energy device. However, the handpiece is rather bulky limiting surgeon's ability to reach into smaller and constrained surgical spaces as well as blocking surgeon's view for precise laser beam aiming. Additional serious disadvantage is that bipolar electrosurgical energy is considered higher risk frequently resulting in unacceptably large extent of coagulation damage to surrounding tissues.

U.S. Pat. No. 8,876,810 describes a method for treatment of benign prostatic hyperplasia using laser energy to both coagulate and incise prostatic tissue. At least two laser sources are used to substantially simultaneously ablate excess tissue and coagulate tissue beyond ablation to provide a near blood-free treatment. As it was suggested in the already referenced earlier U.S. Pat. No. 4,273,127, extent of issue coagulation depends on the wavelength or the frequency of laser radiation because light of different wavelengths is absorbed less or more and thus penetrates into tissue to different depths. Referring back to the method disclosed in U.S. Pat. No. 8,876,810, the second laser source at a different wavelength, penetrating deep into tissue, serves the purpose of expanding tissue coagulation in volume. Laser energies at both wavelengths are substantially simultaneously delivered and large amount of tissue coagulation is induced to stop blood discharge from severed blood vessels and to contain bleeding. The method is relevant to laser treatment of benign prostatic hyperplasia where the objective is to reduce excess prostate tissue by means of ablation and coagulation necrosis of tissue and to prevent severe blood loss during procedure. However, the method is not adequate for precision laser surgeries and microsurgeries in which retaining most of healthy tissue and organ function, and therefore accurate control of extent of tissue coagulation, is most required.

It must be emphasized that the benefits of laser surgery are realized when incising and ablating is performed with a very well controlled small focused laser beam with minimal injury to the surrounding living tissues and critical structures, which must remain healthy. Safeguarding healthy tissues and critical structures is the purpose and major advantage of precision laser surgery. In that regard any extended tissue damage resulting from administering necessary surgical haemostasis should be minimized as well, especially so in microsurgery procedures in the medical fields of otolaryngology, neurosurgery and reproductive surgery. A surgeon needs a laser surgery tool with haemostatic capability allowing control and optimization of haemostatic action and associated with it injury to adjacent tissues, applicable to a diversity of tissues and usable in a variety of surgical procedures. None of the previously disclosed methods and devices appears to have achieved these aims and it is the objective of this invention to address that.

BRIEF SUMMARY OF THE INVENTION

The present invention features a method of incising and ablating living tissues using laser beam and effecting enhanced surgical haemostasis concurrently with incising and ablating. The method does not entail touching tissue with an instrument and is implemented in a single device. Enhanced haemostasis implies arresting bleeding from blood vessels severed by tissue removal with the laser beam to higher degree than conventionally attainable using laser beam alone without separate additional implements for surgical haemostasis, and at the same time minimizing damage to healthy tissues that need to be preserved, limiting the extent of tissue coagulation and necrosis. The method enables adjustment and optimization between acceptable bleeding and extent of haemostasis-related damage to healthy tissues in a variety of tissues and surgical procedures. The method does not rely on specific characteristics of tissue such as pigmentation or high concentration of hemoglobin or myoglobin and applicable to a diversity of living tissues.

The present invention also features surgical laser devices, which operate according to the method of incising and ablating living tissues using laser beam and effecting enhanced surgical haemostasis concurrently with incising and ablating, including an apparatus utilizing flexible fiberoptics for energy delivery and allowing usage of precise laser beam scanning and positioning devices such as laser beam scanners and surgical micromanipulators.

Stated concisely, the present invention provides a method and devices for incising and ablating living tissues with precision of a laser beam and with greater concurrent control of bleeding, yet with less injury to surrounding healthy tissues than what is expected from administering surgical haemostasis separately. According to the present invention, a surgical laser beam to incise and ablate tissue is pulsed and it is highly absorbed in living tissues, as can be characterized by absorption coefficient at least 250 $cm^{-1}$. Enhanced haemostatic action is achieved using along with the surgical laser beam energy thus delivered in pulses, a separately controlled second energy effecting haemostasis, by providing a contact-less means of depositing the second energy in a given spot only into a limited volume of tissue that does not significantly exceed the size of tissue evaporation crater that a single pulse of the surgical laser beam creates. The second energy is delivered, deposited and absorbed into tissue prior to creating tissue evaporation crater with the first surgical laser beam pulse in any and every spot of incising and ablating tissue, thus promoting coagulation shrinkage, constriction and sealing of blood vessels before severing them. Depositing the second energy is continued while the tissue evaporation crater is being developed further with consecutive pulses of the surgical laser beam in the same spot, in advance causing constriction and sealing of blood vessels in the path of the deepening evaporation crater. Such preemptive haemostatic action thus carried out, in combination with the mode of depositing the second energy that limits immediately affected tissue volume in any and every spot of incising and ablating tissue and separately controlling rate of the second energy delivery to tissue between the surgical laser beam pulses, attains stronger and more controlled haemostatic effect with most retention of healthy tissues and their functions. In one embodiment of the present invention the second energy is heat conveyed to tissue by a heated gas jet from a hollow core optical fiber, which also transmits the surgical laser beam. In other embodiments of the present invention the second energy is another laser energy producing haemostatic heat when absorbed into tissue, delivered by the second laser beam at a wavelength chosen specifically according to the requirement of depositing the second energy into a limited tissue volume preemptively and minimizing haemostasis-related damage. The two laser beams are co-propagated coaxially, via free-space optics, articulating arm, flexible optical fiber and via different combinations of all of those. Known devices for precise laser beam steering in laser surgeries, such as laser beam scanners and micromanipulators, can be utilized. All the above advantages and further details of the present invention are apparent in the following detailed description of the invention and the accompanying figures.

DETAILED DESCRIPTION OF THE INVENTION

Figure 1:
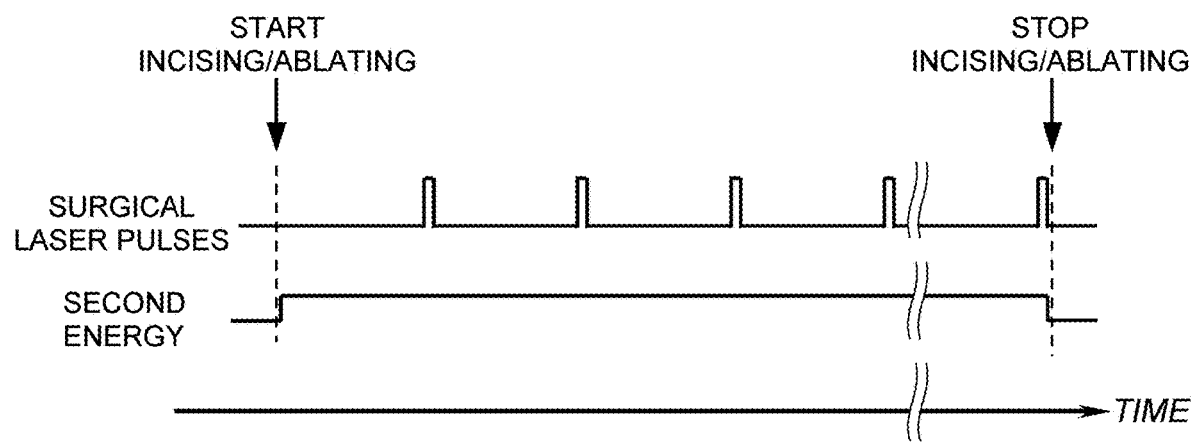
FIG. 1 illustrates the present invention with a basic timing diagram of the surgical laser beam delivery and the second energy delivery for preemptive haemostatic effect.

The readers of this disclosure skilled in the art recognize that various terms describing removal of tissues in surgical laser procedures such as cutting, ablation, excision, incision, vaporization, essentially mean procedure-specific application of tissue incising and ablating with a laser beam. In the context of the present invention surgical incising and ablating with a laser beam is produced by means of precision tissue elimination spot by spot via evaporation or photoablation process, which is further referred to simply as tissue evaporation irrespective of exact process. The surgical laser beam according to the present invention is pulsed and is highly absorbed in living tissues, meaning that absorption of the surgical laser beam pulse results in instant vaporization of tissue in the beam target spot creating a tissue evaporation crater with almost no thermal damage spread to surrounding tissue. Satisfying thus defined criterion for laser beam energy absorption in various living tissues typically requires surgical laser wavelength at which tissue absorption is characterized by absorption coefficient exceeding $250 \text{ cm}^{-1}$, or using an ultrashort pulse laser also known as an ultrafast laser. Ultrafast lasers, usually operating at a wavelength between 0.45 µm and 1.2 µm, deliver energy in trains or bursts of very short pulses of extreme peak power, causing tissue material optical breakdown and evaporation over minimal penetration depth. Therefore in the context of this invention, ultrafast laser beam energy is considered highly absorbed and pulses of pulsed surgical laser beam in this case are bursts or trains of ultrashort pulses. Lasers, which energy is considered highly absorbed in living tissues per the above criterion, also include but not limited to infrared lasers operating at wavelengths of strong water absorption, such as CO2 laser at 10.6 µm and Er:YAG laser at 2.94 µm.

According to the present invention, providing a pulsed surgical laser beam and a means of applying a second energy, via spatially confined delivery of the second energy into tissue in any and every spot of incising and ablating tissue, producing localized thermally induced haemostatic effect preemptively, allows to achieve enhanced haemostatic performance with minimal extension of tissue coagulation and consequential tissue necrosis, further referred to as collateral tissue damage, beyond incision and ablation boundaries. The second energy is heat or other form of energy that produces haemostatic heat when absorbed into tissue. The means of applying the second energy according to the present invention deposits it only into a limited volume of tissue centered on the axis of the surgical laser beam and not substantially larger than tissue evaporation crater resulting from a single pulse of the surgical laser beam in any and every spot of incising and ablating. The meaning of limited volume not substantially larger than the tissue evaporation crater is that the second energy is deposited in a focused manner, immediately affecting only tissue that is to be exposed to the surgical laser beam, and such volume is comparable to the surgical laser spot size laterally and is as shallow as or deeper than the evaporation crater but not significantly larger or deeper as to cause unacceptable collateral tissue damage, which also depends on the amount of the second energy deposited. The second energy is applied necessarily prior to delivery of the surgical laser beam pulses. Heat from the second energy deposited into tissue causes coagulation shrinkage, constriction and sealing of blood vessels in the way of the surgical laser beam before they are cut thus resulting in better control of bleeding yet without extending tissue coagulation much further beyond the evaporation crater being made by the surgical laser beam pulses. A basic timing diagram of the surgical laser pulses and the second energy delivery, depicted in FIG. 1, helps to understand the process. Incising and ablating tissue starts with delivery of the second energy into the target tissue, then following with surgical laser pulse, and then keeping the second energy on between the surgical laser pulses and continuing in that manner until incising and ablating tissue is stopped. FIG. 2 provides further explanation of the method by illustrating only schematically and not to any scale effects produced in a vascular tissue. The four sketches in FIG. 2 depict snapshots of the tissue 201 with blood vessels 202, at four different times as tissue evaporation with the surgical laser beam pulses progresses in a single target spot of incising and ablating tissue. Before the surgical laser pulse creates tissue evaporation crater, the second energy 203 is conveyed and deposited into the tissue at the location coinciding with the surgical laser beam target spot. The second energy is deposited into a limited volume 204, centered on the axis of the surgical laser beam and where the evaporation crater 206 is to be made or extended by the next coming surgical laser pulse 205. Zones of where maximum tissue temperature is reached to cause qualitatively different level of tissue condition are approximately represented in grey tones in the sketches. Below 45° C. tissues typically remain viable. With increase of tissue temperature to 60° C., coagulation commences with irreversible protein denaturation followed by some degree of carbonization, drying and shrinkage of tissue when temperature rises to 90° C.-95° C. Above 90° C. complete cellular destruction occurs. At 100° C. water evaporation commences and that requires considerably more additional heat supplied, in order to actually vaporize water from tissue. If the second energy supplied to tissue between the surgical laser pulses is limited, some but not significant evaporation can occur. Tissue absorption remains sufficiently high for the surgical laser beam from a laser source operating at wavelength of strong water absorption, such as Er:YAG laser or CO2 laser, and from ultrashort pulse lasers, or a laser source operating at wavelength of strong protein absorption, so the efficiency of tissue evaporation with the surgical laser beam pulses is not compromised. Due to protein denaturation and some tissue shrinkage, blood vessels begin to seal before growing tissue evaporation crater 206 severs them. Consecutive laser pulses drill deeper into the tissue and at the same time tissue coagulation induced by the second energy expands also, supporting preemptive haemostatic effect but not extending far beyond tissue evaporation crater 206 because of limited supply of the second energy between the surgical laser pulses and heat conduction and dissipation into the bulk of tissue. The sketches only depict tissue ablation in a single target spot to a certain depth. In practice the surgical laser beam is moved to make an incision or ablate an area to a certain depth, however, the motion of the beam is slow in comparison with the surgical laser beam pulse repetition rate and it takes at least a few surgical laser pulses to attain required depth in a single spot. According to the present invention, the second energy is deposited into the volume of tissue that remains centered on the axis of the laser beam in any and every spot of incising and ablating, the spot location of the second energy application moves together with the surgical laser beam as it will be more evident from further discussion of embodiments of the present invention, and the process works in the same manner as depicted in FIG. 2 for a single target spot. So surgical haemostasis is executed concurrently with incising and ablating tissue in a preemptive and enhanced manner.

Now it is easy to understand that the time interval between the surgical laser pulses, further referred to as pulse period of the surgical laser beam, and the amount of the second energy deposited into tissue in a unit of time, which is determined by rate of delivery of the second energy into tissue, establish the extent of haemostatic coagulation. Because haemostatic heat diffuses out of the limited volume where the second energy is deposited and spreads more into tissue by heat conduction during the time between the surgical laser beam pulses, increasing pulse period of the surgical laser beam while keeping rate of delivery of the second energy low enough to prevent tissue evaporation expands coagulation volume. This way larger blood vessels can be sealed although at the necessary sacrifice of having more collateral tissue damage. Reducing pulse period of the surgical laser beam conversely leads to less spread of heat and coagulation around intended incision and ablation void and less collateral tissue damage. At the same time adjusting pulse energy of the surgical laser beam determines how much tissue evaporation crater grows with each laser pulse, which is kept consistent with progress of haemostatic action. Adjusting pulse period, pulse duration and pulse energy of the surgical laser beam as operational parameters gives control of incising and ablating performance and adjusting rate of delivery of the second energy independently and in conjunction with the surgical laser beam pulse period and pulse energy gives control of haemostatic performance, allowing to balance between the extent of haemostasis needed, tissue cutting and ablation speed and collateral tissue damage as may be requested for a given surgical procedure. Considering thermal relaxation time in soft tissues, pulse period of the surgical laser beam is adjustable in the range between 1 mS and 500 mS and pulse duration of the surgical laser beam is less than 1 mS. Pulse energy of the surgical laser beam depends on characteristics of a particular laser source used for providing it and the beam spot size, skilled in the art can readily determine required pulse energy for a particular surgical laser beam spot size and required incising and ablating performance.

Figure 3A:
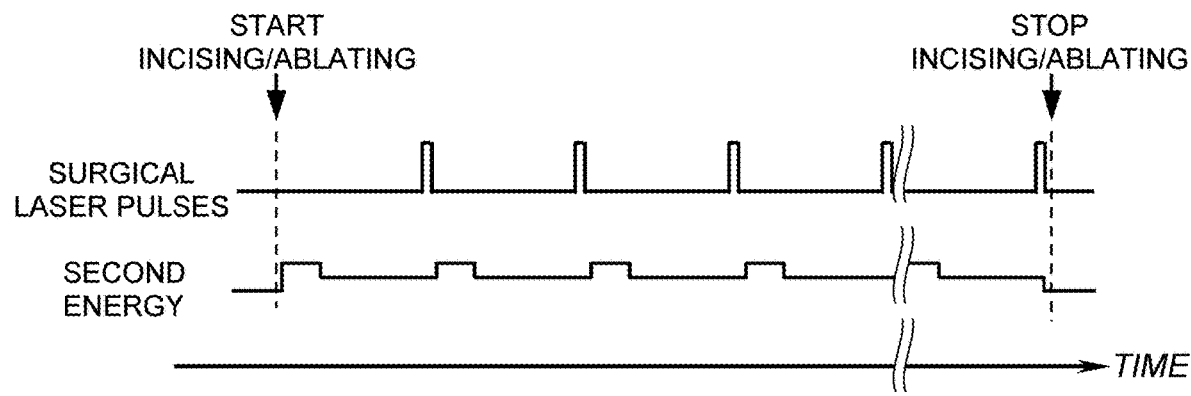
FIG. 3A, FIG. 3B and FIG. 3C present timing diagrams exemplifying the surgical laser beam delivery and the second energy delivery in different embodiments of the present invention.

The second energy delivery can be modulated between consecutive pulses of the surgical laser beam for more precise control of haemostasis induced with the second energy. The second energy delivery can be modulated by amplitude, for example as shown in FIG. 3A, where the second energy is delivered at a higher level initially to quickly raise tissue temperature and then reduced to support haemostatic effect compensating for heat outflow into the bulk of tissue but without risk of overheating the affected tissue volume. The modulation of the second energy delivery can simply be pulsing as exemplified by the timing diagram presented in FIG. 3B. The surgical laser pulses or the second energy pulses or both can also be structured as trains of shorter pulses and pulse-width modulated. An example is given by the timing diagram in FIG. 3C, which shows the surgical laser beam pulses as bursts of shorter pulses and the second energy delivery is pulsed and pulse-width modulated, allowing fine control of rate of delivery of the second energy into tissue and resulting haemostatic effect. In general, modulation of the second energy delivery is according to a certain modulating waveform repeating itself between the trailing edges of the pulses of the surgical laser beam. All parameters defining the modulating waveform are operational parameters for controlling rate of delivery of the second energy. In the context of the present invention, controlling rate of delivery of the second energy means largely preventing tissue evaporation due to the second energy but inducing requested haemostatic performance in regards to collateral tissue damage extent, via either keeping rate of delivery constant or modulating as generally described above. The operational parameters are however determined by specifics of a particular embodiment, depending on the means of applying the second energy, its technical limitations and characteristics of laser source used for providing the surgical laser beam.

When haemostasis is not needed at all, the second energy delivery can be turned off. In that regard, two separate operating controls, for example, two foot pedals as typically used for operating surgical tools, can be given to a surgeon to start and to stop surgical incising and ablating. One to operate with haemostatic action when the second energy is provided along with the surgical laser beam as described above and another to operate the surgical laser beam without the second energy supplied. Skilled in the art should recognize also that the start of incising and ablating and the stop of incising and ablating in the context of the present invention means applying the surgical laser beam and the second energy together as described above to produce a certain surgical outcome in target tissue. The time interval between the start and the stop can be only long enough to deliver a single pulse or just a few pulses of the surgical laser beam under electronic control in response to pressing the operating foot pedal. Applying the surgical laser beam and the second energy together as described above can be continuous in response to pressing the operating foot pedal or can be paused and resumed multiple times. In an embodiment of the present invention utilizing a laser beam scanner, pausing when beam scanner mirrors are moving and resuming when the scanner mirrors are in position may be necessary. Clearly different modes of incising and ablating tissue commonly referred to as "single pulse", "repeat pulse" and "continuous" surgical laser modes, as well as the beam scanner mode with repeated starts and stops are well within the scope of the present invention.

Now that the present invention is overall explained at the fundamental level, examples of particular embodiments and relevant operational parameters, featuring different means of applying the second energy effecting haemostasis preemptively with lesser collateral tissue damage, are further described below but not intended to limit the present invention thereby.

Figure 4:
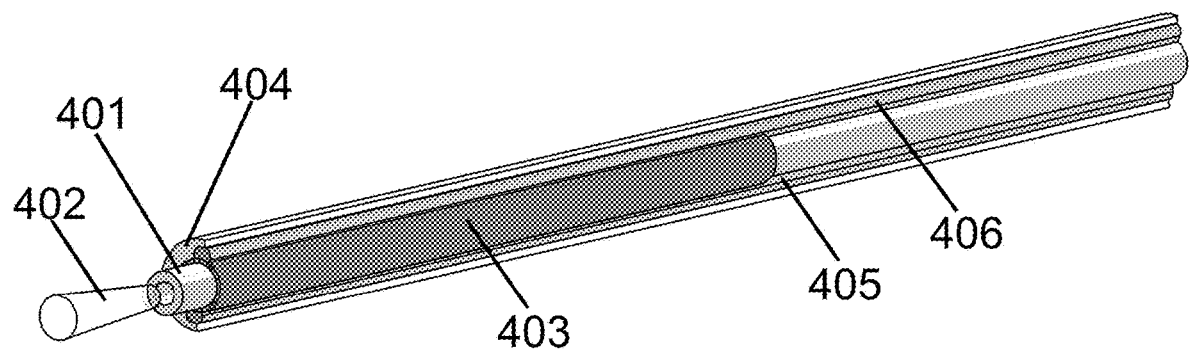
FIG. 4 is an illustration to an embodiment of the present invention utilizing a hollow core fiber for delivery of the surgical laser beam and for producing a heated gas jet coaxial with the surgical laser beam for delivery of the second energy.
Figure 5:
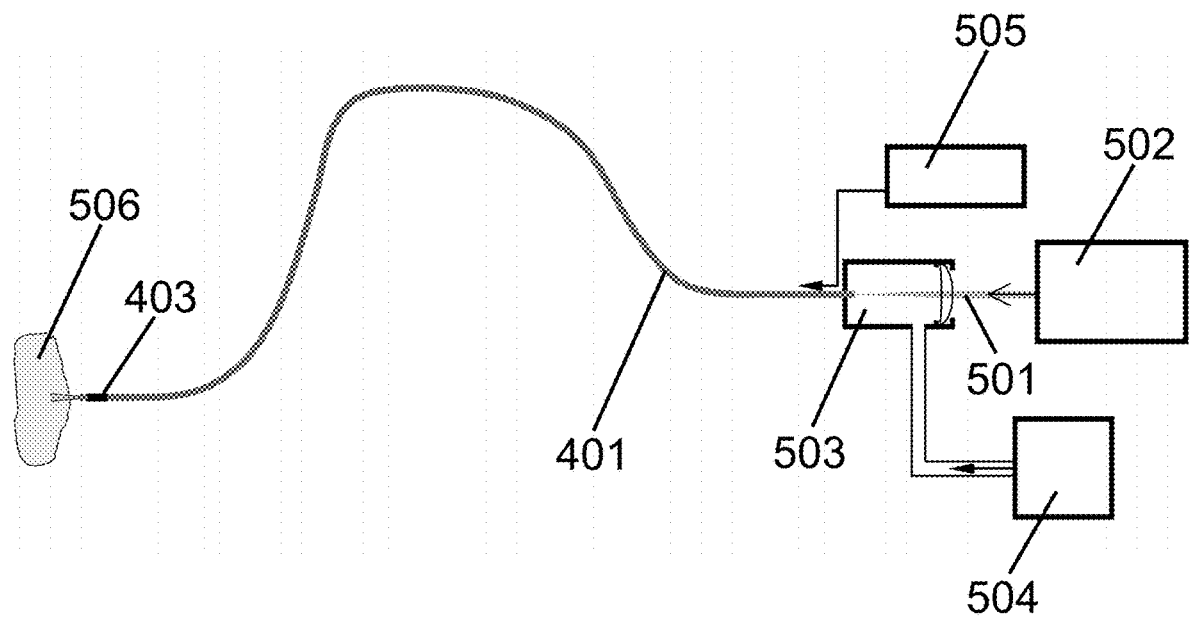
FIG. 5 is a block diagram of an embodiment of the present invention utilizing a hollow core fiber for transmitting the surgical laser beam and supplying the heated gas jet.

One embodiment of the invention is a device utilizing a hollow core optical fiber, also known as hollow waveguide, for delivery of the surgical laser energy. FIG. 4 presents a sectional view of output end portion of the hollow core optical fiber in such device. The hollow core optical fiber 401, normally having core diameter in the range from 200 µm to 600 µm, is used to transmit the surgical laser beam and also to flow inert gas, such as nitrogen or helium. The second energy is heat imparted to tissue by the hot gas jet 402 coming out of the same hollow core optical fiber coaxially with the surgical laser beam. The gas is heated by the heating element 403 over the fiber cladding, embedded into the fiber protective sheath 404 in the output end portion of the fiber. The heating element is a thin film heater deposited over the fiber cladding. It can be a wire-wound heater. The wires 405 and 406, also embedded into the fiber sheath 404, carry electrical current to power the heating element. Hollow core optical fibers such as Polymicro™ hollow waveguides for transmitting laser radiation at near-infrared and infrared wavelengths as well as technologies for making small heaters are well known to the skilled in the art. The heated gas jet is comparable to the surgical laser beam spot size and skilled in the art should recognize that some minimum gas flow is required for that, depending on the hollow fiber core diameter. The second energy is thus delivered to tissue in this embodiment in a focused manner as required. A simple calculation reveals that heating a small volume of soft tissue of 1 mm$^3$ from 37° C. to 100° C. requires approximately 0.25 J of energy transmitted to tissue by the gas jet. Such energy can be delivered in one second by gas at temperature of 130° C. and cooling to 100° C. upon contact with tissue and flowing at 0.4 L/min to 0.6 L/min, depending on the gas used. Nitrogen gas carries a little more heat and lower flow rate of 0.4 L/min can be sufficient, while Helium or Argon require higher flow rates of 0.6 L/min. Because of certain inefficiencies of heat exchange, the maximum gas temperature in a practical device can be in the range of 130° C. to 150° C. and the heating element temperatures up to 160° C. to 180° C. All materials used for hollow core fiber construction, which include silica, silver and silver iodide for optical coatings, polyimide and Tefzer™ for sheath, readily withstand temperatures up to 200° C. On the input end of the hollow core optical fiber a special fiber connector is employed, which provides optical alignment by means of a fiberoptic connector ferrule, electrical connections to power the embedded heating element and a gas seal for allowing gas flow into the hollow core of the fiber by means of O-ring around the ferrule. Such connectors are available and known to the skilled in the art. FIG. 5 presents a block diagram illustrating the device further. The surgical laser beam 501 from the laser source 502 is coupled into the hollow core optical fiber 401 by means of the coupling module 503. The coupling module 503 launches the laser beam and gas, supplied by the gas supply and control module 504, into the hollow core of the fiber 401 as well as it provides electrical connection to power the heating element 403 via the electrical leads embedded in the fiber protective sheath. The gas supply and control module 504 regulates the gas flow through the fiber. The gas heating control module 505 powers the heating element 403 and regulates the gas temperature. The surgical laser beam with the coaxial heated gas jet is directed to the surgical target tissue 506 by manipulating the fiber output end.

Figure 2:
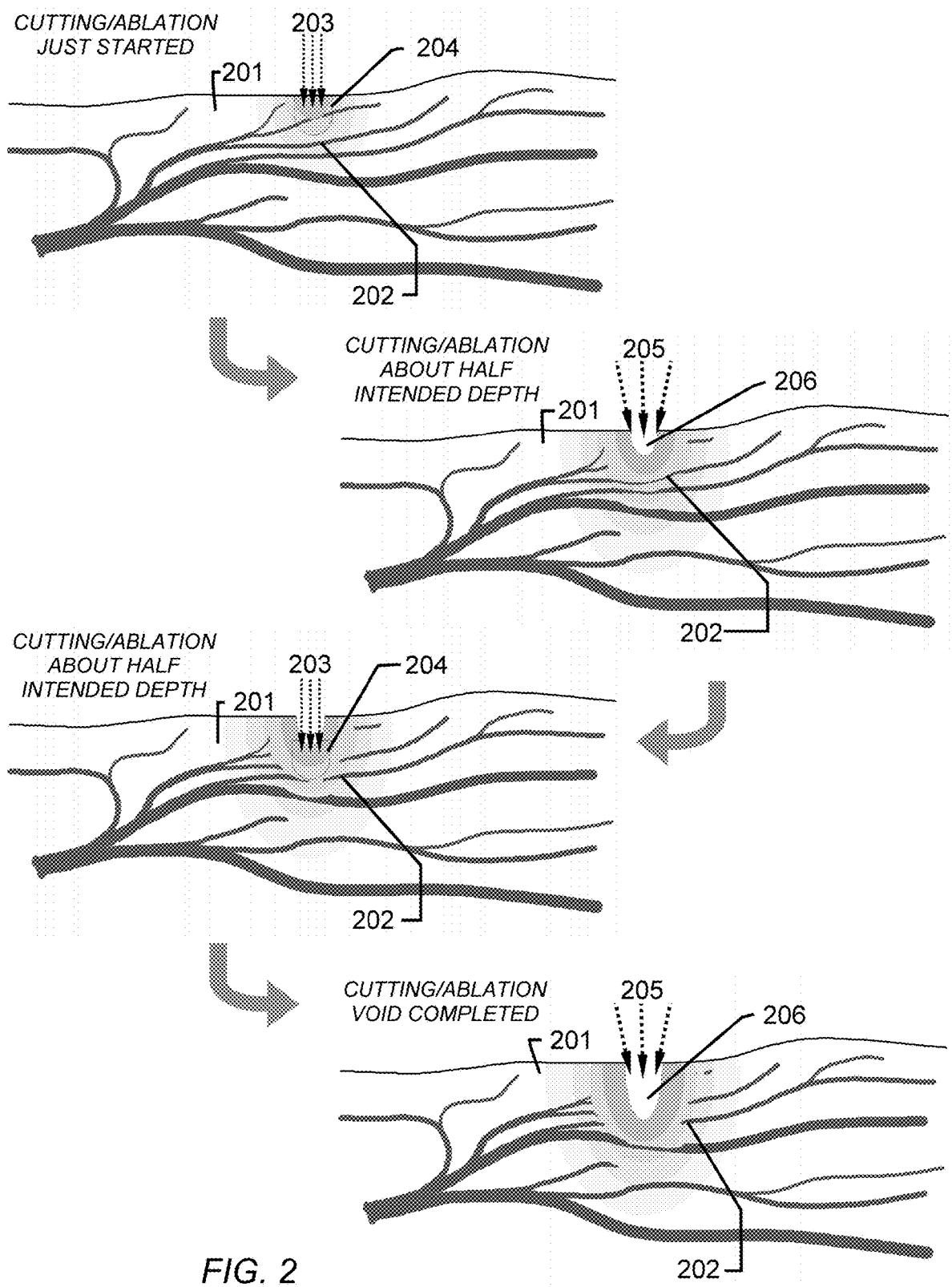
FIG. 2 demonstrates the present invention by showing schematically preemptive haemostatic action in a vascular living tissue.

When the surgical laser beam is requested to perform incising and ablating, the heating element is turned on immediately and prior to the first pulse of the surgical laser beam and the heating element is kept turned on, producing the heated gas jet as long as incising and ablating process continues, as illustrated in FIG. 1, the case of constant rate of delivery of the second energy without modulation. The operation of the gas heating control module 505 is thus synchronized with the operation of the laser source 502 so that the second energy is applied to tissue with the heated gas jet as FIG. 1 shows. The heated gas jet is coaxial with the laser beam and thus heat is transferred to tissue in the same spot where tissue incising and ablating happens. Both the gas jet and the surgical laser beam are directed and moved together by the hollow core optical fiber. The heat transfer to tissue from the heated gas jet happens before the tissue evaporation crater is created and fully completed and touching tissue with the optical fiber tip is not required. When the amount of heat deposited into tissue is limited by adequately chosen gas temperature and gas flow rate and due to heat conduction and dissipation into the bulk of tissue, the extent of haemostatic tissue coagulation is not expanding significantly beyond incision and ablation void. It should be noted that the gas jet continuously reaches into a tissue ablation crater developing with each pulse of the surgical laser beam thus facilitating coagulation in just the tissue enveloping the tissue evaporation crater. Additional benefit of the gas jet is that it clears the target location of smoke and debris. Adjusting the gas jet temperature by controlling the heating element temperature and also adjusting gas flow rate gives control of rate of delivery of the second energy into tissue in this particular embodiment. The heating element temperature and the gas flow rate are operational parameters for adjusting haemostatic performance and the parameter adjustment ranges are 100° C. to 180° C. and 0.2 L/min to 0.8 L/min, respectively. Working distance of one millimeter to a few millimeters between the fiber tip and target tissue is required and it should be noted that both the laser beam and the gas jet diverge with increase of working distance. At larger working distance the gas jet decays but the laser beam also diverges and cannot incise or ablate tissue as effectively.

Altering the surgical laser beam spot size and the area affected by heat transfer from the gas jet by changing the working distance is another way to modify incising and ablating as well as resulting haemostasis.

In a preferred embodiment of the present invention the second energy to effect preemptive haemostasis is another laser energy applied with the second laser beam co-propagated coaxially with the surgical laser beam but of different characteristics and controlled separately. According to the present invention, the second laser beam energy is deposited in any and every spot of incising and ablating into a limited volume of tissue centered on the axis of the surgical laser beam and not substantially larger than tissue evaporation crater that a pulse of the surgical laser beam creates. That means that the maximum of the second laser beam power in the target spot is always centered on the axis of the surgical laser beam, ascertained by coaxial alignment of the laser beams. The spot sizes of the second laser beam and of the surgical laser beam on a surgical target tissue are comparable so that the second energy is delivered into tissue in a focused manner. The surgical laser beam spot size on the target tissue is adjustable and so is the spot size of the second laser beam but always remaining within a factor of two of the spot size of the surgical laser beam. Skilled in the art are generally familiar with optical designs and techniques for aligning laser beams to be coaxial and for controlling and adjusting laser beam spot sizes. Then specific selection of the second laser beam wavelength is necessary. The second laser beam needs to propagate enough into tissue so that no evaporation happens in a superficial layer and tissue is heated to some depth at least the size of tissue evaporation crater to be made. On the other hand, the second laser beam penetration into tissue cannot be too great in order to contain and control collateral tissue damage. According to the present invention, the wavelength of the second laser beam is such that tissue absorption of the second laser beam energy is characterized by absorption coefficient between $10\ cm^{-1}$ and $100\ cm^{1}$.

Figure 3B:
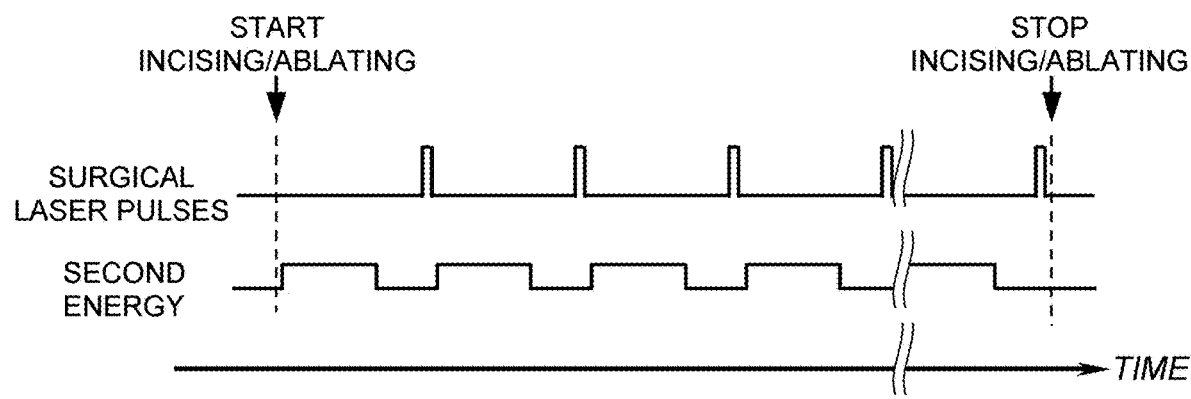
Figure 3C:
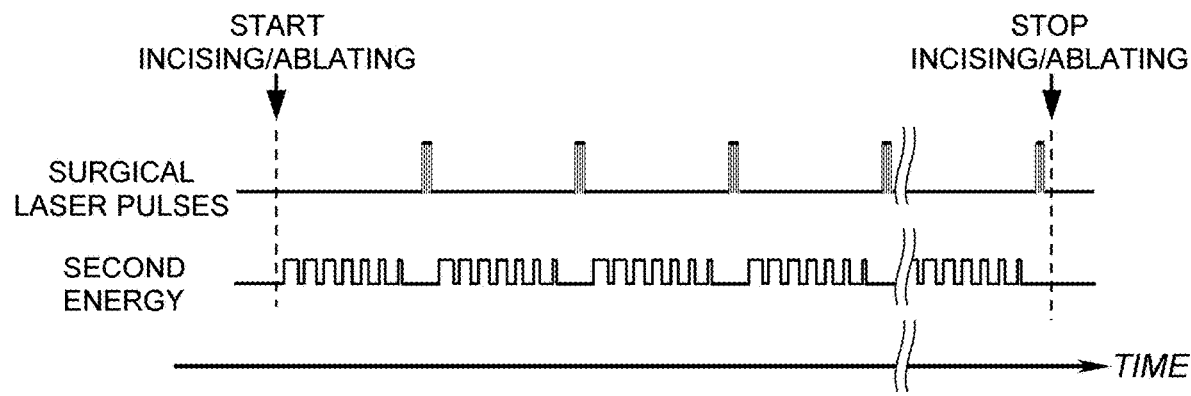

The second laser beam energy is applied before tissue evaporation crater is created and then kept applied while the evaporation crater is being completed with the surgical laser pulses in any and every spot, in accordance with the timing diagrams presented in FIG. 1, or in FIG. 3A, FIG. 3B and FIG. 3C if the second laser beam energy is amplitude-modulated or pulsed or pulsed with pulse-width modulation, respectively. Importantly, operating the surgical laser beam and the second laser beam is coordinated in time, that is, synchronized, to ensure proper timing of the second energy delivery with respect to the pulses of the surgical laser beam. Therefore this embodiment of the present invention necessarily includes a controller module for synchronized operation of both laser beams, which functions as a master driver for laser sources supplying the surgical laser beam and the second laser beam triggering laser emissions at the correct times when the surgical laser pulse period is adjustable as an operational parameter. If a laser beam scanner is utilized to position and scan the laser beams on the surgical target to incise and ablate in a predetermined geometrical pattern, synchronized operation of the laser beams with the scanner mirrors is also necessary and the controller module has a means of controlling laser beam scanner in that case. Skilled in the art should be familiar with how such controllers can be designed.

The volume of affected tissue may expand both laterally and in depth due to heat conduction but it remains limited by the amount of energy supplied by the second laser beam between the consecutive pulses of the surgical laser beam.

The average power level of the second laser beam and modulation parameters, if the second laser beam power is modulated, are set to ensure that tissue evaporation due to the second laser beam is negligible and tissue removal happens with pulses of the surgical laser beam. Heating 1 mm$^3$ volume of soft tissue from 37° C. to 100° C. requires approximately 0.25 J of energy and considering some heat dissipation into the bulk of tissue, 0.3 W to 0.5 W average power of the second laser beam delivered into tissue is sufficient to produce haemostatic tissue coagulation at a rate of 1 mm$^3$ per second. Lower average power of the second laser beam and longer exposure, which is determined by the pulse period of the surgical laser beam, allows heat to propagate further into tissue, expanding haemostatic coagulation. Modulating the second laser beam power between consecutive pulses of the surgical laser beam gives more control of rate of delivery of the second energy. Skilled in the art readily understand that different variations of modulating waveform controlling the second laser beam power can be entertained and more fine control is possible in this embodiment without deviating from the present invention. Operational parameters for controlling rate of delivery of the second energy into tissue in this embodiment therefore include average power of the second laser beam and all relevant parameters defining the power-modulating waveform. The average laser beam power to tissue is in the range from zero when no haemostatic effect is needed and up to 5 W, depending on the beam spot size, larger spot sizes requiring more average power, and on the cutting and ablation speed needed.

Figure 6:
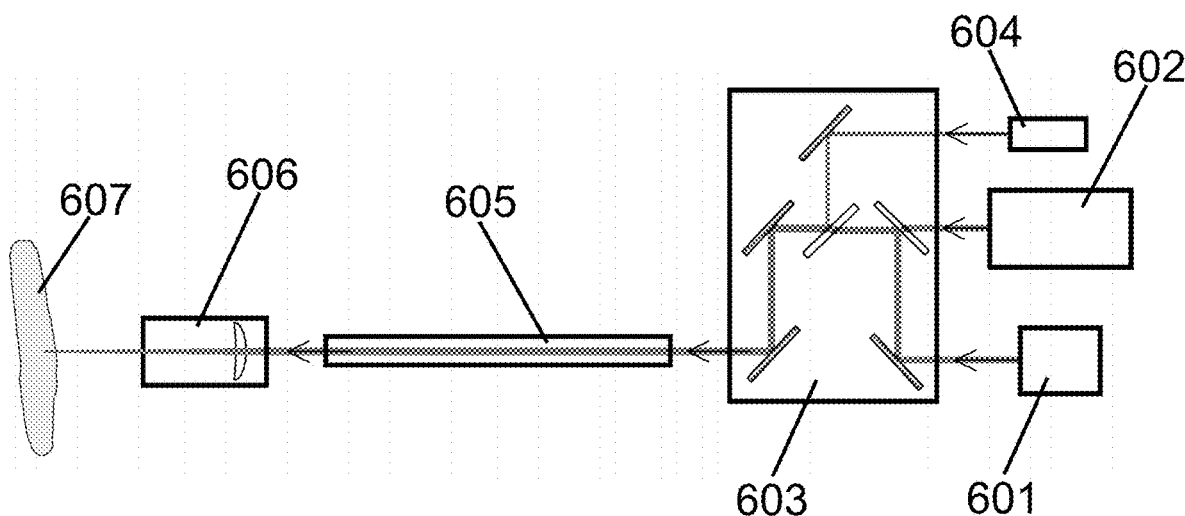
FIG. 6 is a block diagram of an exemplary optical arrangement in an embodiment of the present invention with the second laser beam for applying the second energy.

FIG. 6 presents a block diagram of an exemplary optical arrangement in an embodiment of the present invention with the second laser beam for applying the second energy effecting surgical haemostasis, showing schematically delivery of the surgical laser beam and the second laser beam to a surgical target tissue. The second laser beam provided by the ancillary laser source 601, which can include one or more lasers, is merged with the surgical laser beam provided by the main laser source 602, which can also include one or more lasers, in the optical alignment and beam-compounding module 603. Skilled in the art are knowledgeable of techniques for aligning laser beams to co-propagate coaxially as a single compounded laser beam using regular and dichroic mirrors and possibly fiberoptic beam combiners. The module 603 can also include optics for adding a low power aiming beam to co-propagate coaxially in the compounded laser beam. An aiming laser 604, operating at visible wavelength, usually green or red, provides the aiming beam in that case. The compounded laser beam is transmitted to a surgical site via beam delivery conduit 605, which is an articulating arm or an optical fiber. A laser beam manipulation device 606 is often required to direct and focus the compounded laser beam on the surgical target tissue 607, allowing to adjust the beam spot size of the surgical laser beam and the beam spot size of the second laser beam on the target tissue 607. A surgical micromanipulator or a handpiece with a focusing optics, connected to an articulating arm, are often used as the beam manipulation device 606. If an optical fiber is the beam delivery conduit 605, the compounded laser beam out of the optical fiber can be used without any optics. The beam delivery conduit is operational at both the surgical laser beam and the second laser beam wavelengths, and at the aiming beam wavelength. Using articulating arm presents no technical limitation on the choice of laser wavelength for either the surgical laser beam or the second laser beam because broadband metallic silver mirrors, which reflect light in a very wide range of wavelengths from 0.45 µm to 20 µm, are normally used in articulating arms. When an optical fiber is used as the beam delivery conduit 605, the choice of the laser wavelengths may be more limited depending on the optical fiber spectral transmission. Many optical fiber types for laser beam delivery with core diameters ranging from 50 µm to 600 µm and possibly up to 1 mm for IR wavelengths have wide spectral transmission in multimode regime with low transmission loss over relatively short distance, at most a few meters needed in laser surgery applications. Solid core fluoride glass fibers transmit from 0.5 µm to 4 µm to 4.5 µm, depending on exact fluoride glass composition and solid core sapphire fibers transmit from 0.4 µm to 4.5 µm. Hollow core optical fibers also known as hollow waveguides are available with wide spectral transmission that can be optimized for specific wavelengths in the range from 1.2 µm to 12 µm by adjusting the fiber core diameter and reflective optical coatings on the inside of the fiber hollow core. Solid core low-OH silica fibers transmit from 0.4 µm to 2.3 µm and can be used in an embodiment with ultrafast laser supplying the surgical laser beam and a diode laser supplying the second laser beam at about 1.9 µm wavelength. Any optics used in the path of the compounded laser beam needs to be operational at both wavelengths with acceptable differences in regards to transmission or reflection losses and focusing characteristics. Many optical elements operate in a wide range of wavelengths, for example, ZnSe optics can be used for laser beams at wavelengths in a wide range from 0.6 µm to 14 µm. Antireflective coatings can be designed to work at two or more wavelengths and appropriate optical design is exercised to ensure required beam spot sizes and the beam spot size adjustment ranges. Spherical and parabolic silver mirrors are advantageous because their focusing performance is independent of wavelength and in fact such mirrors are often used in surgical micromanipulators. The overall transmission through the beam delivery conduit 605 and all optical elements in the optical path to the surgical target tissue 607 are optimized for the surgical laser beam wavelength while somewhat lower transmission of the second laser beam and the aiming beam is compensated for by using higher power from the laser sources.

Figure 7:
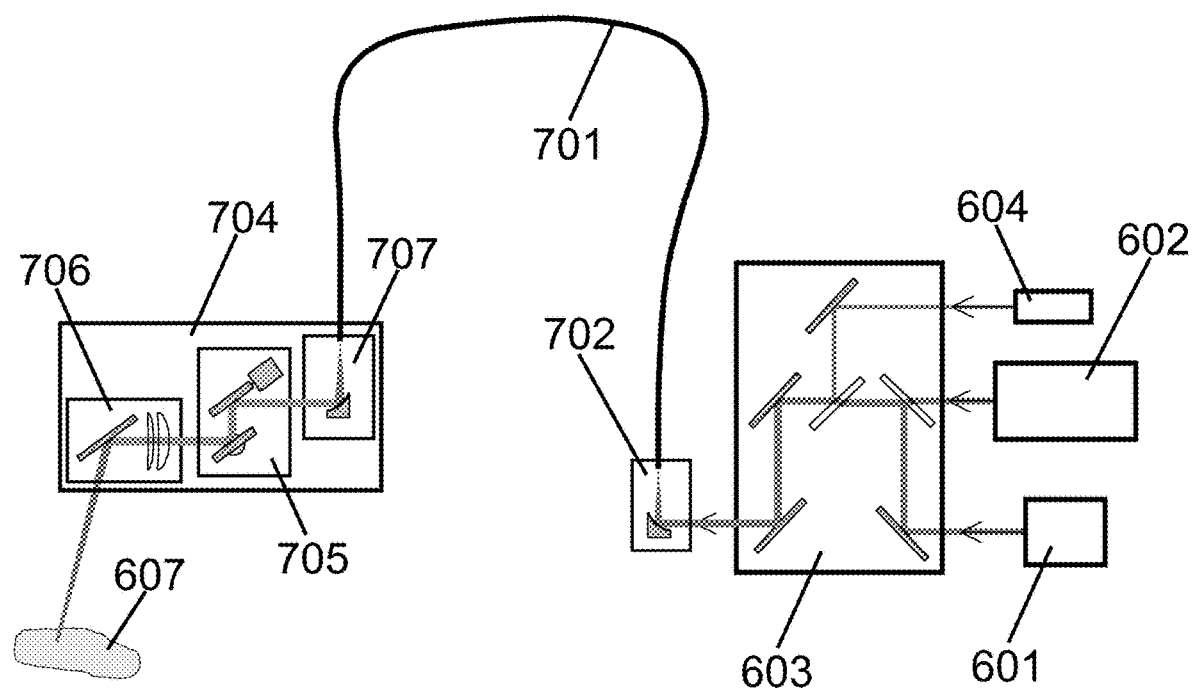
FIG. 7 is a block diagram of an exemplary optical arrangement in a preferred embodiment of the present invention with the second laser beam for applying the second energy, in which a flexible optical fiber and a laser beam scanning and positioning device are used.

Given the general scheme presented in FIG. 6, it is easy to see that a number of different ways to make an optical arrangement for using multiple laser sources together, aligning and compounding their laser beams to co-propagate coaxially to a surgical site and ensuring required spot sizes on the surgical target tissue, can be devised by the skilled in the art. FIG. 7 presents a block diagram of an optical arrangement similar to the one shown in FIG. 6, but in a preferred embodiment utilizing specifically an optical fiber as the beam delivery conduit with necessary fiber-coupling optics and additional implements for precise laser beam scanning and positioning. The optical fiber 701 is from the fiber types discussed above with wide spectral transmission. The laser beams, compounded in the optical alignment and beam-compounding module 603, are launched into the optical fiber 701 by means of a fiber-coupling module 702. Coming out of the optical fiber 701, the laser beams are directed to the surgical target tissue 607 with a laser beam scanning and positioning device 704. The laser beam scanning and positioning device 704 includes a laser beam scanner 705 and a surgical micromanipulator 706. The scanner 705 is used to produce precise surgical incision and ablation patterns while the micromanipulator 706 is used for accurate beam positioning, focusing and adjustment of beam spot size on the surgical target tissue. In order to operate with the laser beams coming out of the optical fiber 701, the laser beam scanning and positioning device 704 is equipped with an optical collimator element 707 designed to work with the laser beams of different wavelengths. The optical collimator element 707 can utilize silver off-axis parabolic mirror. The laser beam scanning and positioning device 704 can alternatively include the laser beam scanner 705 with a handpiece with a focusing optics.

It should be appreciated that the present invention is generally applicable for incising and ablating a diversity of living tissues. Because water is main ingredient of all living soft tissues, a surgical laser beam highly absorbed in water is used in a preferred embodiment, for example, CO2 laser operating at 10.6 µm wavelength or Er:YAG laser operating at or near 2.94 µm. Er:YAG laser is advantageous because its wavelength coincides with the peak of water absorption and its penetration depth is the least, giving most precise surgical incising and ablating of tissue. Ultrashort pulse laser, also called ultrafast laser, can be used for providing the surgical laser beam. Ultrafast lasers deliver energy in very short pulses of extreme peak power causing tissue material optical breakdown and evaporation in any kind of tissue irrespective of exact tissue absorption at the laser wavelength. Therefore, an ultrafast laser is also preferred for supplying the surgical laser beam to incise and ablate a diversity of living tissues. Regarding haemostatic capability, applying the second energy to tissue is sufficiently independent of exact tissue kind if the second energy is heat transferred to tissue by a heated gas jet. In a preferred embodiment utilizing the second laser beam, applicability to a diversity of tissues can be achieved by selection of the second laser beam wavelength to rely on tissue water absorption as well, but in the near-IR, where water absorption is weaker. A publication in Journal of Biomedical Optics, Vol. 22(3), p. 035009 (2017), incorporated herein by reference, presents detailed measurements of tissue absorption at wavelengths from 0.35 µm to 2.6 µm. Absorption of various tissues at wavelengths between 1.4 µm and 2.1 µm is well characterized by absorption coefficients in the range between 10 $cm^{-1}$ and 100 $cm^{-1}$, with absorption maxima corresponding to water absorption peaks at 1.45 µm and 1.95 µm. The second laser beam wavelength can therefore be advantageously chosen to be between 1.4 µm and 2.1 µm.

The embodiments of the present invention described above demonstrate different means of applying second energy effecting preemptive controlled haemostasis concurrently with incising and ablating tissue and minimizing collateral tissue damage from haemostatic effect. It is to be understood however that the present invention is not limited to these exact embodiments, various modifications may be considered therein by those skilled in the art without departing from essential principles and the scope of the present invention as defined in the appended claims.

What is claimed is:

1. A method of incising and ablating living tissues, comprising the steps of:
   providing a surgical laser beam to incise and ablate living tissue, wherein said surgical laser beam is pulsed and is highly absorbed in a variety of living tissues;
   providing a means of applying a second energy effecting surgical haemostasis in a variety of living tissues, wherein said means of applying requires no touching tissue with a surgical instrument and said means of applying deposits said second energy in any and every spot of incising and ablating into volume of tissue centered on axis of said surgical laser beam, said volume of tissue being limited by spot size of said surgical laser beam within a factor of two and by penetration depth of said second energy into tissue, said penetration depth being not greater than 1 mm;
   controlling pulse period, pulse duration, pulse structure and pulse energy of said surgical laser beam to furnish said pulse duration of said surgical laser beam less than 1 mS and said pulse period of said surgical laser beam between 1 mS and 500 mS;
   controlling rate of delivery of said second energy into tissue independently and in conjunction with controlling said pulse period and said pulse energy of said surgical laser beam to furnish tissue coagulation for haemostasis without tissue removal during period of time given by said pulse period of said surgical laser beam;
   applying said second energy with said means of applying before tissue evaporation crater is created with the first pulse of said surgical laser beam in any and every spot of incising and ablating; and
   continuing to apply said second energy with said means of applying while tissue evaporation crater is being developed with the pulses of said surgical laser beam in any and every spot of incising and ablating.

2. A method of incising and ablating living tissues according to claim 1, wherein said step of providing said surgical laser beam to incise and ablate living tissues further comprises the step of selecting wavelength of said surgical laser beam to be between 2.7 µm and 3.2 µm or to be between 9 µm and 11 µm.

3. A method of incising and ablating living tissues according to claim 1, wherein said step of providing said surgical laser beam to incise and ablate living tissues further comprises the step of selecting an ultrashort pulse laser also known as an ultrafast laser to supply said surgical laser beam.

4. A method of incising and ablating living tissues according to claim 1, wherein:
   said step of providing said surgical laser beam to incise and ablate living tissues further comprises the step of delivering said surgical laser beam to a surgical target tissue via a hollow core optical fiber also known as a hollow waveguide;
   said second energy is heat delivered into tissue with a heated gas jet;
   said step of providing said means of applying said second energy further comprises the steps of:
      flowing gas through said hollow core optical fiber;
      letting said gas jet out of said hollow core fiber coaxially with said surgical laser beam;
      providing a heating element for raising temperature of said gas to produce said heated gas jet, wherein said heating element is disposed in output end portion of said hollow core optical fiber;
   said step of controlling said rate of delivery of said second energy into tissue further comprises the steps of:
      regulating flow rate of said gas;
      controlling temperature of said heating element;
   said step of applying said second energy with said means of applying comprises the step of switching said heating element on prior to the first pulse of said surgical laser beam; and
   said step of continuing to apply said second energy with said means of applying comprises the step of keeping said heating element switched on during and between consecutive pulses of said surgical laser beam.

5. A method of incising and ablating living tissues according to claim 1, wherein:

said second energy is laser energy delivered into tissue with a second laser beam;
said step of providing said means of applying said second energy further comprises the steps of:
selecting wavelength of said second laser beam, wherein absorption of said second laser beam energy in a variety of living tissues is characterized by absorption coefficient between 10 cm$^{-1}$ and 100 cm$^{-1}$;
co-propagating said second laser beam coaxially with said surgical laser beam to a surgical target tissue;
said step of controlling said rate of delivery of said second energy into tissue further comprises the steps of:
controlling average power level of said second laser beam;
modulating power of said second laser beam according to a modulating waveform repeating between the trailing edges of consecutive pulses of said surgical laser beam and controlling parameters that define said modulating waveform, or keeping said power of said second laser beam steady;
said step of applying said second energy with said means of applying comprises the step of switching said second laser beam on prior to the first pulse of said surgical laser beam; and
said step of continuing to apply said second energy with said means of applying comprises the step of keeping said second laser beam switched on during and between consecutive pulses of said surgical laser beam.

6. A method of incising and ablating living tissues according to claim 1, wherein:
said step of providing said surgical laser beam to incise and ablate living tissue further comprises the step of delivering said surgical laser beam to a surgical target tissue via an optical fiber;
said second energy is laser energy delivered into tissue with a second laser beam;
said step of providing said means of applying said second energy further comprises the steps of:
selecting wavelength of said second laser beam, wherein absorption of said second laser beam energy in a variety of living tissues is characterized by absorption coefficient between 10 cm$^{-1}$ and 100 cm$^{1}$;
delivering said second laser beam to said surgical target tissue via said optical fiber;
said step of controlling said rate of delivery of said second energy into tissue further comprises the steps of:
controlling average power level of said second laser beam;
modulating power of said second laser beam according to a modulating waveform repeating between the trailing edges of consecutive pulses of said surgical laser beam and controlling parameters that define said modulating waveform, or keeping said power of said second laser beam steady;
said step of applying said second energy with said means of applying comprises the step of switching said second laser beam on prior to the first pulse of said surgical laser beam; and
said step of continuing to apply said second energy with said means of applying comprises the step of keeping said second laser beam switched on during and between consecutive pulses of said surgical laser beam.

7. A method of incising and ablating living tissues according to claim 6, wherein said optical fiber is selected from the group consisting of solid core fluoride glass fibers of various fluoride glass compositions, solid core sapphire fibers, solid core germanium oxide glass fibers, solid core silica fibers including low-OH silica fibers, and hollow core optical fibers also known as hollow waveguides.

8. A method of incising and ablating living tissues according to claim 5, wherein said step of selecting wavelength of said second laser beam further comprises the step of selecting wavelength of said second laser beam to be between 1.4 µm and 2.1 µm.

9. A method of incising and ablating living tissues according to claim 6, wherein said step of selecting wavelength of said second laser beam further comprises the step of selecting wavelength of said second laser beam to be between 1.4 µm and 2.1 µm.

10. A method of incising and ablating living tissues according to claim 6, further comprising the step of directing both said surgical laser beam and said second laser beam out of said optical fiber to a surgical target tissue by means of a laser beam scanning and positioning device, wherein said laser beam scanning and positioning device comprises an optical collimator element and a laser beam scanner.

11. A surgical laser device for incising and ablating living tissues with concurrent enhanced surgical haemostasis according to the method of claim 1, comprising:
a main laser source providing said surgical laser beam;
an ancillary laser source providing a second laser beam, wherein absorption of said second laser beam in a variety of living tissues is characterized by absorption coefficient between 10 cm$^{-1}$ and 100 cm$^{1}$;
an optical arrangement providing a compounded laser beam of two or more coaxially aligned constituent beams, a first constituent beam being said surgical laser beam and a second constituent beam being said second laser beam, wherein beam spot sizes of said first constituent beam and of said second constituent beam on a surgical target tissue being adjustable and comparable to each other within a factor of two, said optical arrangement comprising a beam-compounding module, a beam delivery conduit and a beam manipulation device; and
a controller module capable of synchronized operation of said main laser source and said ancillary laser source, wherein laser emission from said ancillary laser source always precedes emission of a laser pulse from said main laser source by an interval defined by said pulse period of said surgical laser beam.

12. A surgical laser device for incising and ablating living tissues with concurrent enhanced surgical haemostasis according to the method of claim 1, comprising:
a laser source providing said surgical laser beam;
a hollow core optical fiber also known as a hollow waveguide, wherein said hollow core fiber has a heating element disposed over fiber cladding in output end portion of said hollow core optical fiber, said heating element connected to heating element wires disposed along length of said hollow core optical fiber and individually insulated within a protective sheath of said hollow core optical fiber, and a fiber connector disposed on input end of said hollow core optical fiber for optical coupling of laser radiation, coupling of gas and electrical connection of said heating element wires;
a gas supply and control module capable of controlling gas flow through said hollow core optical fiber;
a gas heating control module capable of regulating temperature of said heating element synchronized with operation of said main laser source; and
a coupling module capable of launching said surgical laser beam into said hollow core optical fiber, establishing gas flow through said hollow core optical fiber and connecting electrically said heating element wires via said fiber connector to said gas heating control module.

13. A surgical laser device for incising and ablating living tissues with concurrent enhanced surgical haemostasis according to claim 11, wherein wavelength of said main laser source is between 2.7 µm and 3.2 µm or is between 9 µm and 11 µm.

14. A surgical laser device for incising and ablating living tissues with concurrent enhanced surgical haemostasis according to claim 12, wherein wavelength of said laser source is between 2.7 µm and 3.2 µm or is between 9 µm and 11 µm.

15. A surgical laser device for incising and ablating living tissues with concurrent enhanced surgical haemostasis according to claim 11, wherein said main laser source is an ultrashort pulse laser, also known as an ultrafast laser, producing laser pulses as trains of ultrashort pulses.

16. A surgical laser device for incising and ablating living tissues with concurrent enhanced surgical haemostasis according to claim 11, further comprising:

an aiming beam laser providing an aiming beam, wherein said aiming beam being third constituent beam of said compounded laser beam.

17. A surgical laser device for incising and ablating living tissues with concurrent enhanced surgical haemostasis according to claim 11, wherein wavelength of said ancillary laser source is between 1.4 µm and 2.1 µm.

18. A surgical laser device for incising and ablating living tissues with concurrent enhanced surgical haemostasis according to claim 11, wherein said beam delivery conduit comprises an optical fiber selected from the group consisting of solid core fluoride glass fibers of various fluoride glass compositions, solid core sapphire fibers, solid core germanium oxide glass fibers, solid core silica fibers including low-OH silica fibers, and hollow core optical fibers also known as hollow waveguides.

19. A surgical laser device for incising and ablating living tissues with concurrent enhanced surgical haemostasis according to claim 11, wherein said beam manipulation device comprises a laser beam scanner.

* * * * *